United States Patent [19]
Abe et al.

[11] Patent Number: 5,958,915
[45] Date of Patent: Sep. 28, 1999

[54] ANTIBACTERIAL COMPOSITION FOR ORAL ADMINISTRATION

[75] Inventors: Kenichi Abe; Masato Ota; Hiroyuki Yamaguchi, all of Yokohama; Chikako Murakami, Kawasaki; Toshihiro Kikkoji, Yokohama, all of Japan

[73] Assignee: Meiji Seika Kaisha, Ltd., Japan

[21] Appl. No.: 09/051,318

[22] PCT Filed: Oct. 14, 1996

[86] PCT No.: PCT/JP96/02967

§ 371 Date: Apr. 8, 1998

§ 102(e) Date: Apr. 8, 1998

[87] PCT Pub. No.: WO97/13516

PCT Pub. Date: Apr. 17, 1997

[30] Foreign Application Priority Data

Oct. 13, 1995 [JP] Japan .................................. 7-265847

[51] Int. Cl.⁶ ................................................ A61K 31/545
[52] U.S. Cl. .......................................... 514/206; 514/974
[58] Field of Search ...................................... 514/206, 974

[56] References Cited

FOREIGN PATENT DOCUMENTS 2-225423  9/1990  Japan ............................. A61K 47/42

*Primary Examiner*—Kimberly Jordan
*Attorney, Agent, or Firm*—Larson & Taylor

[57] ABSTRACT

A new, antibacterial composition for use in oral administration is now provided, which composition comprises a mixture of Cefditoren pivoxyl with a water soluble casein salt. This composition has a reduced bitter taste of Cefditoren pivoxyl and also has improved properties regarding the rate and concentration of dissolution of Cefditoren pivoxyl in water and a ratio of dissolution out of Cefditoren pivoxyl into water. This composition further can attain a high absorbability of the Cefditoren component at the digestive tubes upon oral administration thereof. In this composition, the ratio (by weight) of Cefditoren pivoxyl to the casein salt added may preferably be in a range of 1:0.1 to 1:4. By further addition of a water-soluble polyphosphoric acid salt to the composition, the composition can prevent a ratio of dissolution out into water of the Cefditoren pivoxyl component being decreased when the composition was stored under severe conditions.

16 Claims, 5 Drawing Sheets

ANTIBACTERIAL COMPOSITION FOR ORAL ADMINISTRATION

This application is a 371 of PCT/JP96/02967, filed Oct. 14, 1996.

TECHNICAL FIELD

This invention relates to a new antibacterial composition of Cefditoren pivoxyl for use in oral administration, which has a reduced or minimized bitter taste to patients upon oral administration thereof and is quickly soluble in water and also attaining a high absorbability of the Cefditoren component at the digestive tubes, and which composition comprises a mixture of Cefditoren pivoxyl with a proportion of a pharmaceutically acceptable and water-soluble casein salt. This invention also relates to a new antibacterial composition of Cefditoren pivoxyl for use in oral administration, which has a reduced or minimized bitter taste to patients upon oral administration thereof and is quickly soluble in water and also can attain a high absorbability of the Cefditoren component at the digestive tubes and is further capable of maintaining a high rate of dissolution out of its Cefditoren pivoxyl component into water even after a storage of the composition was done at an elevated temperature, and which composition comprises a mixture of Cefditoren pivoxyl with a proportion of the water-soluble casein salt and a proportion of a pharmaceutically acceptable and water soluble polyphosphoric acid salt. This invention further embraces a method for reducing the bitter taste of Cefditoren pivoxyl and enhancing the rate of dissolution of Cefditoren pivoxyl into water, which method comprises mixing Cefditoren pivoxyl with a proportion of a pharmaceutically acceptable and water-soluble casein salt.

BACKGROUND ART

Cefditoren is a cephem compound represented by the following formula (A):

and named as (+)-(6R,7R)-7-[(Z)-2-(2-aminothiazol-4-yl)-2-methoxyiminoacetamido]-3-[(Z)-2-(4-methylthiazol-5-yl)-ethenyl]-8-oxo-5-thia-1-azabicyclo[4.2.0]oct-2-ene-2-carboxylic acid. This cephem compound having the generic name "Cefditoren" is also nominated as 7-[2-methoxyimino-2-(2-aminothiazol-4-yl)acetamido]-3-[2-(4-methylthiazol-5-yl)vinyl]-3-cephem-4-carboxylic acid(syn-isomer, cis-isomer) in the specifications of Japanese patent No. 1698887(Japanese patent publication "Kokoku" No. Hei-3-64503 published on Oct. 7, 1991), U.S. Patent No. 4,839,350 and European patent No. 0175610. A pivaloyloxymethyl ester of Cefditoren, where the 2-carboxyl group of said cephem compound has been esterified with pivaloyloxymethyl group for the purpose of enhancing the absorbability of the cephem compound via the digestive tubes upon the oral administration thereof (the absorbability of the cephem compound in this sense is referred to simply as "oral absorbability" sometime hereinafter),is such a pro-drug which is known under a generic name "Cefditoren pivoxyl". This pro-drug compound is represented by the following formula (B):

and has a chemical name "(−)-(6R,7R)-7-[(Z)-2-(2-aminothiazol-4-yl)-2-methoxyiminoacetamido]-3-[(Z)-2-(4-methylthiazol-5-yl)ethenyl]-8-oxo-5-thia-1-azabicyclo[4.2.0] oct-2-ene-2-carboxylic acid 2,2-dimethylpropionyloxymethyl ester".

It is generally deemed that when such a medicinal compound (called simply as a drug hereinafter) which is essentially in the form of an acid has been esterified at the acid group thereof with an ester-forming group, the resulting ester compound can gain an enhanced or improved lipophilicity through the esterification so as to increase the membrane permeability of the drug at the digestive tubes, whereby the resulting ester compound can attain an enhancement in its absorbability at the digestive tubes, namely an enhanced oral absorbability much than that of the original drug of the acid form. As be known well, however, the absorbability of a drug at the digestive tubes is closely co-related to the solubility of said drug in water. The esterified drug, owing to its enhanced lipophilicity, can have its reduced characteristics that relate to the solubilities of the drug in respect of its wettability with water, its dispersibility in water, and others. Therefore, some problems have occurred in that the esterification of a medicinal compound is not necessarily able to achieve an enhancement or improvement in the absorbability of the compound at digestive tubes to a satisfactory extent.

Cefditoren, which is the antibacterially active species, does not exhibit the bitter taste by itself upon oral administration thereof, whilst Cefditoren pivoxyl of the ester form is the pro-drug which can exhibit a strong bitter taste objectionably to patients who receive oral administration of it. Thus, there is a strong demand that the bitter taste of Cefditoren pivoxyl is to be reduced or minimized to such an extent that the oral administration of Cefditoren pivoxyl would be acceptable by patients. On the other hand, to solve certain problems concerning the oral absorbability of Cefditoren pivoxyl, there has been proposed several years ago such a formulation in which Cefditoren pivoxyl is mixed with a cyclodextrin or a hydroxypropyl cellulose, one of water-soluble cellulose derivatives of high molecular weights (Japanese patent application first publication "Kokai" Nos. Hei-1-268637 and Hei-7-17866). However, the addition of cyclodextrin to Cefditoren pivoxyl can bring about the formation of a water-soluble complex of Cefditoren pivoxyl with cyclodextrin, with involving a great increase in the solubility of Cefditoren pivoxyl itself in water and thereby enhancing highly the bitter taste which is attributable just to the drug, Cefditoren pivoxyl. The highly enhanced bitter taste of this drug which is brought about by the addition of cyclodextrin can lead to a great trouble to patients who receive oral administration of the above-mentioned formulation comprising the mixture of Cefditoren pivoxyl with cyclodextrin.

While, in order to improve the oral absorbability of Cefditoren pivoxyl by the addition of hydroxypropyl cellulose thereto, it is necessary that the amount of hydroxypropyl cellulose as added to and mixed with Cefditoren pivoxyl is increased considerably much more than such usual amounts of hydroxypropyl cellulose which was conventionally used as a binding agent in an amount of 1% by weight or more or less on the basis of the weight of the whole formulation comprising Cefditoren pivoxyl and the hydroxypropyl cellulose added as the conventional binding agent. When a considerably increased amount of hydroxypropyl cellulose has been added to and mixed with Cefditoren pivoxyl, the function of the added hydroxypropyl cellulose to act as the binding agent can display strongly.

In order to suppress the strong binder-function of the hydroxypropyl cellulose as incoporated in said considerably increased amount, it is necessary to also increase considerably the amount of a disintegrator to be added to Cefditoren pivoxyl, so that the disintegratability of the tablet preparation or granule preparation as formulated therefrom can be kept at a reasonable degree. This necessity would lead to another problems such that the resulting tablet preparation or granule preparation should be of a bulky volume and should be difficult to be taken by patients orally. Besides, the addition of hydroxypropyl cellulose to Cefditoren pivoxyl can bring about a problem such that the water component present in the preparations comprising the mixture of Cefditoren pivoxyl with hydroxypropyl cellulose is difficult to be removed therefrom and hence the water content of said preparations cannot be minimized, so that the water content can disadvantageously result in a possible decrease in the stability of the active drug component present in said preparations. Furthermore, the method of mixing Cefditoren pivoxyl with hydroxypropyl cellulose is essentially not able to reduce the bitter taste of Cefditoren pivoxyl itself to a satisfactorily full extent.

Whilst, various methods for masking or reducing the bitter taste of medicinal compositions or formulations containing a drug compound having a bitter taste are generally known hitherto. For instance, the known methods of masking the bitter taste of a drug compound embraces a method of coating the surfaces of the particles of the drug compound with a coat-film. This method of coating the particle surfaces of the drug compound with the coat-film can suitably be applied to the preparations of the tablet form. However, when this method is effected for the preparations of the granule form or the fine granule form, there can be involved such drawbacks that the surfaces of the granules or the fine granules so coated become rough and give objectionable feelings to mouth and tongue, and that the steps for the production of the granules or the fine granules so coated with the film are complicated, and so on. A method of mixing a sweetening agent or a flavoring agent with the drug having a bitter taste may also be employed, but this method is not effective to a sufficient extent. Accordingly, there remains now an outstanding demand to provide a new and much more effective measure for solving the problems that the bitter taste of a drug having a bitter taste should be reduced or minimized to an extent acceptable to patients.

DISCLOSURE OF THE INVENTION

The present inventors have now made extensive researches in an attempt to provide a new and orally administrable preparation of Cefditoren pivoxyl which contains Cefditoren pivoxyl as the active drug ingredient but does not exhibit any objectionably strong bitter taste to patients upon the oral administration thereof and which can also give a high absorbability of the Cefditoren component at the digestive tubes, namely an enhanced oral absorbability of the Cefditoren component. As a result of the extensive researches, the present inventors have now found that a preparation comprising a mixture of Cefditoren pivoxyl with a prescribed proportion of a water-soluble casein salt can have an improved dispersibility of said preparation in water and thereby can attain a remarkable increase in the rate of dissolution of the Cefditoren pivoxyl component from the preparation into water, as well as a remarkable increase in the concentration of the Cefditoren pivoxyl component which may be obtained by the dissolution of said component into water for a predetermined period of time, and that consequently, said preparation comprising the mixture of Cefditoren pivoxyl with the prescribed proportion of the water-soluble casein salt can give an enhancement in the oral absorbability of the Cefditoren component over the oral administration of single Cefditoren pivoxyl alone when said preparation is administered via the oral route. The casein salt as incoporated in said preparation comprising the mixture of Cefditoren pivoxyl with the casein salt does have such a nature that the casein salt will form casein micell when said casein salt is placed into water. It is presumed by the present inventors that the formation of the micell of the casein in water does affect the Cefditoren pivoxyl component advantageously in the above-mentioned points that there are obtained the enhanced dispersibility of said preparation in water, the enhanced rate of the dissolution of the Cefditoren pivoxyl component from the preparation into water and the enhanced concentration of said Cefditoren pivoxyl component dissolved in water which is attainable by the dissolution of said component into water for a predetermined time, as well as the reduced bitter taste of the Cefditoren pivoxyl component.

Further, the present inventors have also found that the incorporation of the water-soluble casein salt in said preparation is able to reduce greatly or minimize the bitter taste of Cefditoren pivoxyl itself. On the basis of these findings, the present inventors have now accomplished the present inventions which will be described hereinafter in more details.

In a first aspect of this invention, therefore, there is provided an antibacterial composition of Cefditoren pivoxyl for use in oral administration and having a reduced bitter taste and having an enhanced dispersibility of the composition in water and an enhanced rate of dissolution of Cefditoren pivoxyl component in water, characterised in that the composition comprises a mixture of Cefditoren pivoxyl with a proportion of a pharmaceutically acceptable and water-soluble casein salt.

The casein salt which is incorporated in the composition of this invention may be any salt of known and water-soluble casein salt materials and is not limited to an especial sort of the casein salt. However, sodium caseinate and pottasium caseinate are preferred as the water soluble casein salt, because they have a high solubility in water. More preferably, the composition of this invention may contain such a sodium caseinate which has been obtained by using a fresh skimmed milk as the raw material, separating a casein curd therefrom, neutralizing the casein curd and then spray-drying the resultant milk protein material having reduced flavors and color. It is allowable that the casein salt used in the composition of this invention contains a minor amount or small amount of casein itselff.

In the composition of this invention, the amount of the casein salt as incorporated therein may be such that the proportion of the casein salt is 0.1 proportions or greater per 1 proportion of Cefditoren pivoxyl on the weight basis, in order to ensure that the bitter taste of Cefditoren pivoxyl is reduced significantly. However, the ratio by weight of Cefditoren pivoxyl to the casein salt in the composition may preferably be in a range of 1:0.4 to 1:4, more particularly in a range of 1:0.6 to 1:2, in order to ensure that the composition of this invention has a high dispersibility in water of the preparations made of said composition and also an enhanced rate of dissolution of the Cefditoren pivoxyl component into water, as well as an increased percentage of dissolution out of the Cefditoren pivoxyl component from the composition into water for a predetermined time period of eg. 60 minites. Here, if the proportion of the casein salt incorporated in the composition is less than 0.1 proportions per 1 proportion of Cefditoren pivoxyl, this composition can not exhibit the desired high dispersibility of the resulting preparation and the desired high percentage of dissolution out of the drug component into water. On the other hand, if the proportion of the casein salt incorporated in the composition exceed the upper limit thereof, and namely is greater than 4 proportions per 1 proportion of Cefditoren pivoxyl, there occur such problems that the preparation made from this composition would be of an excessively bulky volume and be difficult to be taken by patients orally. For these reasons, it is desirable that the ratio by weight of Cefditoren pivoxyl to the casein salt is in a range of 1:0.4 to 1:4 as indicated above.

Upon the manufacture of the orally administrable preparations from the composition according to this invention, there are not imposed any special limitations on the formulation type of the resulting preparation and the available methods of manufacturing said preparation. For instance, it is feasible to manufacture by any conventional methods an orally administrable preparation such as tablets, granules, dry syrups, powders, capsules and the like, from the composition of this invention.

Furthermore, it is feasible and preferable that the composition of this invention further contains one or more excipients such as sucrose, lactose, D-mannitol, potato starch, xylitol, D-sorbitol and the like, as well as one or more disintegrators such as sodium carboxymethyl starch, crospovidon, croscarmellose sodium, carmellose calcium, a low substituted hydroxypropyl cellulose, a partly pregelatinied starch, crystalline cellulose and the like, for the purposes to further improve the disintegratability and dispersibility of the preparations made from the composition of this invention. The amount of the disintegrator(s) as further incorporated in the composition may be in a range of 0 to 45% by weight on the weight basis of the whole composition or the oral preparations made of said composition. When occassion demands, the composition of this invention may optionally contain further one or more pharmaceutically acceptable additives such as binder, sweetening agent, flavoring agent, lubricant, antiseptic, taste-improver, coloring agent and the like.

Further, the present inventors have continued to make investigations on the storage stability of the antibacterial composition according to the first aspect of this invention.

And, the present inventors have then discovered that, when the composition of the first aspect of this invention has been stored for a long time of eg. 2 to 3 months at an elevated temperature of eg., 40° C., the rate of dissolution of the Cefditoren pivoxyl component into water from the composition so stored, as well as the concentration of the Cefditoren pivoxyl component in water attainable by the dissolution out of said component into water from the so stored composition for a predetermined time can be lowered unacceptably, as compared with those obtainable at the time immediately after when the composition of the first aspect of this invention has just been prepared by mixing the necessary ingredients, namely Cefditoren pivoxyl, the casein salt and the optionally required additive(s) with each other.

To solve this problem, the present inventors have done further researches and have get a success to find out the following. Thus, the present inventors have now found that, when a proportion of a pharmaceutically acceptable and water-soluble polyphosphoric acid salt is additionally incorporated into the composition of the first aspect of this invention, and when the composition so prepared with the incorporation of the water-soluble polyphosphoric acid salt was stored for a period of 3 months at an elevated temperature of 40° C., the same composition after the storage at 40° C. for the long time does neither show any unacceptable decrease in the rate of dissolution of the Cefditoren pivoxyl component into water from the stored composition, nor any unacceptable decrease in the concentration of the Cefditoren pivoxyl component in water which is attainable by the dissolution out of said component into water from the stored composition for the predetermined time.

In a second aspect of this invention, therefore, there is provided an antibacterial composition of Cefditoren pivoxyl for use in oral administration and having a reduced bitter taste and having an enhanced dispersibility of the composition and an enhanced rate of dissolution of the Cefditoren pivoxyl component in water and also capable of maintaining a high rate of dissolution of the Cefditoren pivoxyl component into water after storage of the composition at an elevated temperature, characterized in that the composition comprises a mixture of Cefditoren pivoxyl with a proportion of a pharmaceutically acceptable and water-soluble casein salt and a proportion of a pharmaceutically acceptable and water-soluble polyphosphoric acid salt.

In the composition according to the second aspect of this invention, the casein salt present in the composition may preferably be sodium caseinate and potassium caseinate, similarly to the composition of the first aspect of this invention, and also the ratio by weight of the Cefditoren pivoxyl component to the casein salt is preferably in a range of 1:0.4 to 1:4, more particularly in a range of 1:0.6 to 1:2.

The composition according to the second aspect of this invention may preferably contain the casein salt and the water-soluble polyphosphoric acid salt in such proportions that the ratio by weight of the casein salt to the polyphosphoric acid salt is in a range of 1:0.02 to 1:0.06, more particularly in a range of 1:0.02 to 1:0.05, in order to ensure that the composition of the second aspect of this invention can exhibit and keep the desired good properties for the dissolution of the Cefditoren pivoxyl component into water from the composition even after the storage of the composition at elevated temperatures for a long time.

Thus, by adjusting the proportion of the polyphosphoric acid salt present in the composition of the second aspect of this invention so that the ratio by weight of the casein salt to the polyphosphoric acid salt is in the range of 1:0.02 to 1:0.06, the same composition can be capable of maintaining such characteristics that its original high rate of dissolution of the Cefditoren pivoxyl component into water from the composition and the originally high concentration of the Cefditoren pivoxyl component in water which is attainable by the dissolution of said component into water from the composition for the predetermined time can be prevented from being decreased unacceptably less than those as obtained by the composition just produced, even when the same composition had been stored at the elevated temperature for the long time.

The water-soluble polyphosphoric acid salt which is incorporated in the composition of the second aspect of this invention may most preferably be a pure sodium or potassium tripolyphosphate. But, it may be a commercially available sodium or potassium polyphosphate which is usually composed of sodium or potassium tripolyphosphate as the main constituent along with minor quantities of sodium or potassium pyrophosphate, sodium or potassium trimetaphosphate and highly polymerised sodium or potassium phosphate.

When the composition of the second aspect invention contains the casein salt and the polyphosphoric acid salt at such a ratio of the former to the latter in a range of 1:0.02 to 1:0.04 by weight, the disintegratability of the same composition is improved slightly over that of such composition not containing the polyphosphoric acid salt. While, if the proportion of the polyphosphoric acid salt as incorporated is greater than the upper limit of 0.06 proportions per 1 proportion of the casein salt, the disintegratability of the composition containing such excessive proportion of the polyphosphoric acid salt can be decreased, because the binding power of the polyphosphoric acid salt itself increases too much undesirably. Furthermore, it is found that the presence of the polyphosphoric acid salt incorporated in the composition of this invention does not substantially affect adversely the function of the casein salt component to reduce the bitter taste of the Cefditoren pivoxyl component in the composition.

The composition of the second aspect of this invention may be produced in any known manner, for example, by simply mixing with Cefditoren pivoxyl, the casein salt, the optionally incorporatable additive(s) and the polyphosphoric acid salt with each other to give a uniform powdery mixture. When the same composition is to be prepared in the form of granules, it is possible to mix Cefditoren pivoxyl with the casein salt and the optionally incorporatable additive(s), then add to the resulting powdery mixture an aqueous solution of the polyphosphoric acid salt, and finally shape the resulting admixture into granules by any known wet-granulating method. The granules so obtained may then be shaped into tablets by a conventional tableting method. It is also possible that a uniform powdery mixture comprising Cefditoren pivoxyl, the casein salt and the optional additives is first prepared and then shaped into granules by a known wet-granulating method, followed by drying the granules and then spraying the dried granules with an aqueous solution of the polyphosphoric acid salt, and finally dehydrating the granules.

The composition of the second aspect of this invention, of course, may contain additionally and optionally one or more additives such as disintegrator, excipient, lubricant and the like, which may be the same as those mentioned hereinbefore for the first aspect of this invention.

Moreover, as will be evident from the descriptions given hereinbefore of the first aspect of this invention, to mix Cefditoren pivoxyl with a proportion of a pharmaceutically acceptable and water-soluble casein salt is able to reduce the bitter taste of Cefditoren pivoxyl itself to an extent acceptable by patients at the oral administration of Cefditoren pivoxyl and to bring about some improvements in the properties for the dissolution of Cefditoren pivoxyl into water.

In a further aspect of this invention, therefore, there is provided a method for reducing the bitter taste of Cefditoren pivoxyl and enhancing the rate of dissolution of Cefditoren pivoxyl into water as well as the concentration of Cefditoren pivoxyl in water attainable by the dissolution into water for a predetermined period of time, which method comprises mixing Cefditoren pivoxyl with a proportion of a phamaceutically acceptable and water-soluble casein salt at a ratio by weight of Cefditoren pivoxyl to the casein salt in a range of 1:0.4 to 1:4, preferably in a range of 1:0.6 to 1:2, and thereby forming a uniform mixture of Cefditoren pivoxyl with the casein salt.

BEST MODES FOR WORKING THE INVENTION

This invention in the first aspect thereof is now illustrated with reference to the following Examples 1 to 9 and Test Examples 1 to 4. However, these Examples do not limit this invention in any way.

EXAMPLE 1

Cefditoren pivoxyl (130 g) was mixed well with sodium caseinate (520 g) to give a uniform powdery mixture, which was then kneaded with addition thereto of an appropriate amount of a purified water as prepared according to the rules of the Japanese Pharmacopeia, 13th-Edition. The so kneaded mixture was then granulated by a conventional wet-granulating method to afford fine granules which may be orally administrable as a powder.

EXAMPLES 2 to 8

Uniform powdery mixtures were prepared by mixing powders of Cefditoren pivoxyl, sodium caseinate, D-mannitol and croscarmellose sodium with each other in different proportions of the respective constituents for the different seven formulations as indicated in Table 1 given below.

These powdery mixtures were respectively added with appropriate amounts of water and then granulated by a conventional wet-granulating method. The granules so obtained were further admixed with magnesium stearate as a lubricant and then shaped into tablets by compression in a conventional manner. Thereby, there were manufactured tablets having 7 different formulations where the weight ratio of Cefditoren pivoxyl to sodium caseinate in each formulation was 1:0.1, 1:0.2, 1:0.4, 1:0.6, 1:0.8, 1:1.0 and 1:2.0, respectively. For each formulation, the tablets having the same formulation were obtained at a scale of 1000 tablets.

The formulations of the tablets so produced are detailed in Table 1 below.

TABLE 1

| Constituents | Formulations (quantities (mg) of the constituents per one tablet) | | | | | | |
| --- | --- | --- | --- | --- | --- | --- | --- |
| | Example 2 | Example 3 | Example 4 | Example 5 | Example 6 | Example 7 | Example 8 |
| Cefditoren pivoxyl | 130 | 130 | 130 | 130 | 130 | 130 | 130 |
| Sodium caseinate | 13 | 26 | 52 | 78 | 104 | 130 | 260 |
| D-mannitol | 9.5 | 11 | 12 | 14 | 15 | 17 | 25 |
| Croscarmellose sodium | 75 | 80 | 95 | 110 | 120 | 135 | 150 |
| Magnesium stearate | 2.5 | 3 | 3 | 3 | 3 | 3 | 4 |
| Total quantities of constituents | 230 | 250 | 292 | 335 | 372 | 415 | 569 |
| Ratio by weight of Cefditoren pivoxyl to sodium caseinate | 1:0.1 | 1:0.2 | 1:0.4 | 1:0.6 | 1:0.8 | 1:1.0 | 1:2.0 |

EXAMPLE 9

A uniform powdery mixture comprising 130 g of Cefditoren pivoxyl, 390 g of sodium caseinate and 480 g of D-mannitol was prepared and then granulated by a conventional wet-granulating method, so that there were produced such granules of the formulation that the granules contained the respective constituents in the proportions as indicated below, per 1000 mg of the granules.

| | |
| --- | --- |
| Cefditoren pivoxyl | 130 mg |
| Sodium caseinate | 390 mg |
| D-mannitol | 480 mg |
| Total | 1000 mg |

REFERENTIAL EXAMPLE 1

A uniform powdery mixture comprising 130 g of Cefditoren pivoxyl, 130 g of β-cyclodextrin and 5 g of hydroxypropyl methylcellulose was prepared, and then added with an appropriate amount of water and subsequently kneaded well. The resulting admixture so kneaded was granulated by a known wet-granulating method to give the granules. The resulting granules were further admixed with a homogeneous powder mixture which was separately prepared by mixing 10 g of a low substituted hydroxypropyl methylcellulose with 150 g of citric acid well. (By the way, the citric acid could not be incorporated directly into the said granules due to its incompatibility, since it could deteriorate the drug compound if it was brought into direct contact with the drug compound.) The mixture so obtained was then added and mixed with 6 g of magnesium stearate, and the resulting admixture was shaped into tablets by compression by a known tableting method. In this way, there were produced such tablets (Comparative sample 1; according to the prior art invention of the Japanese patent application first publication "Kokai" No. Hei-1-268637) which had such formulation that each tablet contained the respective constituents in the proportions as indicated below.

| | |
| --- | --- |
| Cefditoren pivoxyl | 130 mg |
| β-cyclodextrin | 130 mg |
| Hydroxypropyl methylcellulose | 5 mg |
| Low substituted hydroxypropyl methylcellulose | 10 mg |

-continued

| | |
| --- | --- |
| Citric acid | 150 mg |
| Magnesium stearate | 6 mg |
| Total | 431 mg |

REFERENTIAL EXAMPLE 2

A uniform powdery mixture comprising 130 g of Cefditoren pivoxyl, 64 g of D-mannitol and 95 g of croscarmellose sodium was prepared, and then added and mixed with an appropriate amount of water and subsequently granulated by a conventional wet-granulating method. The resulting granules were further added and mixed with 3 g of magnesium stearate, and the resulting mixture was shaped into tablets by compression by a known tableting method. In this way, there were produced such tablets (Comparative sample 2), which had the formulation that each tablet contained the respective constituents in the proportions as indicated below.

| | |
| --- | --- |
| Cefditoren pivoxyl | 130 mg |
| D-mannitol | 64 mg |
| Croscarmellose sodium | 95 mg |
| Magnesium stearate | 3 mg |
| Total | 292 mg |

REFERENTIAL EXAMPLE 3

A uniform powdery mixture comprising 130 g of Cefditoren pivoxyl and 390 g of hydroxypropyl cellulose (L-type) was prepared, and then dissolved in 3 kg of dichloromethane added thereto. In the resulting solution was further added and suspended 480 g of D-mannitol. The suspension so obtained was heated in an evaporator to remove the organic solvent therefrom. The residue obtained was ground and sieved to collect the particles of appropriate sizes. Thereby, there were produced such granules (Comparative sample 3), which had the formulation that the granules contained the respective constituents in the proportions as indicated below, per 1000 mg of the granules.

| | |
|---|---|
| Cefditoren pivoxyl | 130 mg |
| Hydroxypropyl cellulose | 390 mg |
| D-manniotl | 480 mg |
| Total | 1000 mg |

Next, with reference to the following Test Examples 1 to 4, it is demonstrated in details that the composition of Cefditoren pivoxyl according to the first aspect of this invention can exhibit such advantageous characteristics that the rate of dissolution of the Cefditoren pivoxyl component into water from the composition is enhanced, that the concentration of the Cefditoren pivoxyl component dissolved in water from the composition which is attainable by the dissolution of the drug component into water from the composition for a predetermined time is also enhanced, that the oral absorbability of the Cefditoren component attainable by the composition of this invention is high, and that the bitter taste of the preparation made of the present composition is reduced.

TEST EXAMPLE 1

11 powders (fine granules) composed of Cefditoren pivoxyl and sodium caseinate at different ratios, more particularly such 11 powders (the fine granules) composed of mixtures of Cefditoren pivoxyl and sodium caseinate but having different ratios by weight between Cefditoren pivoxyl and sodium caseinate (namely, A/B ratio) of 1:0.0, 1:0.1, 1:0.2, 1:0.3, 1:0.4, 1:0.5, 1:0.6, 1:0.8, 1:1, 1:2 and 1:4, respectively, were produced in the same manner as in Example 1 above by the wet-granulation method according the first aspect of this invention. Among the 11 powder so produced, however, the one powder containing no sodium caseinate (having the A/B ratio of 1:0.0) is a comparative sample not according to this invention.

Each one of these powders was added in such an amount equivalent to 100 mg of Cefditoren pivoxyl into a volume (100 ml) of water at 37° C. in a cylindrical vessel having a hemispheric bottom. While the drug powder added and the water pool present in the vessel were then immediately stirred at 37° C. by means of a blade-type stirrer, the concentration (mg/ml) of the drug compound (Cefditoren pivoxyl) dissolved in the water phase was measured with lapse of time from the addition of the powder for 60 minutes. Percentages of the dissolution of said drug compound into water were evaluated with lapse of time, as assumed that the percentages of the dissolution of Cefditoren pivoxyl in water would be 100% at the time when a complete dissolution out of the whole Cefditoren pivoxyl into water from the powder was achieved.

More particularly, the percentages of the dissolution of Cefditoren pivoxyl dissolved in water were calculated by the following equation at the time when the measurement was made.

Percentages of the dissolution of the drug compound=b/a×100 wherein b means the concentration (mg/ml) of Cefditoren pivoxyl dissolved in water at the time when the measurement was made,and a means a theoretically maximum concentration (mg/ml) of the Cefditoren pivoxyl dissolved in water at the time when the whole Cefditoren pivoxyl present in the powder would have completely dissolved into water out of the powder.

The test results obtained are shown in Table 2 below.

TABLE 2

| | Percentages (%) of the dissolution of drug compound Lapse time (min.) | | | | | | |
|---|---|---|---|---|---|---|---|
| Test samples | 0 | 1 | 3 | 5 | 10 | 30 | 60 |
| Sample No. 1 (comparative) (A/B ratio, 1:0.0) | 0 | 29.39 | 45.01 | 53.31 | 58.15 | 61.38 | 61.92 |
| Sample No. 2 (A/B ratio, 1:0.1) | 0 | 50 | 57.88 | 61.28 | 63.55 | 68.46 | 66.03 |
| Sample No. 3 (A/B ratio, 1:0.2) | 0 | 48.24 | 57.94 | 59.79 | 62.39 | 64.23 | 64.25 |
| Sample No. 4 (A/B ratio, 1:0.3) | 0 | 60.12 | 63.46 | 65.63 | 66.88 | 69.07 | 69.77 |
| Sample No. 5 (A/B ratio, 1:0.4) | 0 | 72.89 | 79.46 | 81.02 | 80.4 | 80.03 | 79.07 |
| Sample No. 6 (A/B ratio, 1:0.5) | 0 | 76.38 | 79.37 | 79.99 | 80.62 | 79.92 | 80.88 |
| Sample No. 7 (A/B ratio, 1:0.6) | 0 | 84.62 | 88 | 88.48 | 90.61 | 88.86 | 88.42 |
| Sample No. 8 (A/B ratio, 1:0.8) | 0 | 85.26 | 89.2 | 90.06 | 91.25 | 91.02 | 90.58 |
| Sample No. 9 (A/B ratio, 1:1) | 0 | 85.05 | 88.94 | 91.13 | 92.23 | 91.89 | 90.74 |
| Sample No. 10 (A/B ratio, 1:2) | 0 | 84.76 | 89.41 | 91.86 | 91.52 | 90.63 | 91.07 |
| Sample No. 11 (A/B ratio, 1:4) | 0 | 85.11 | 90.25 | 90.64 | 92.38 | 92.26 | 91.58 |

Figure 1:
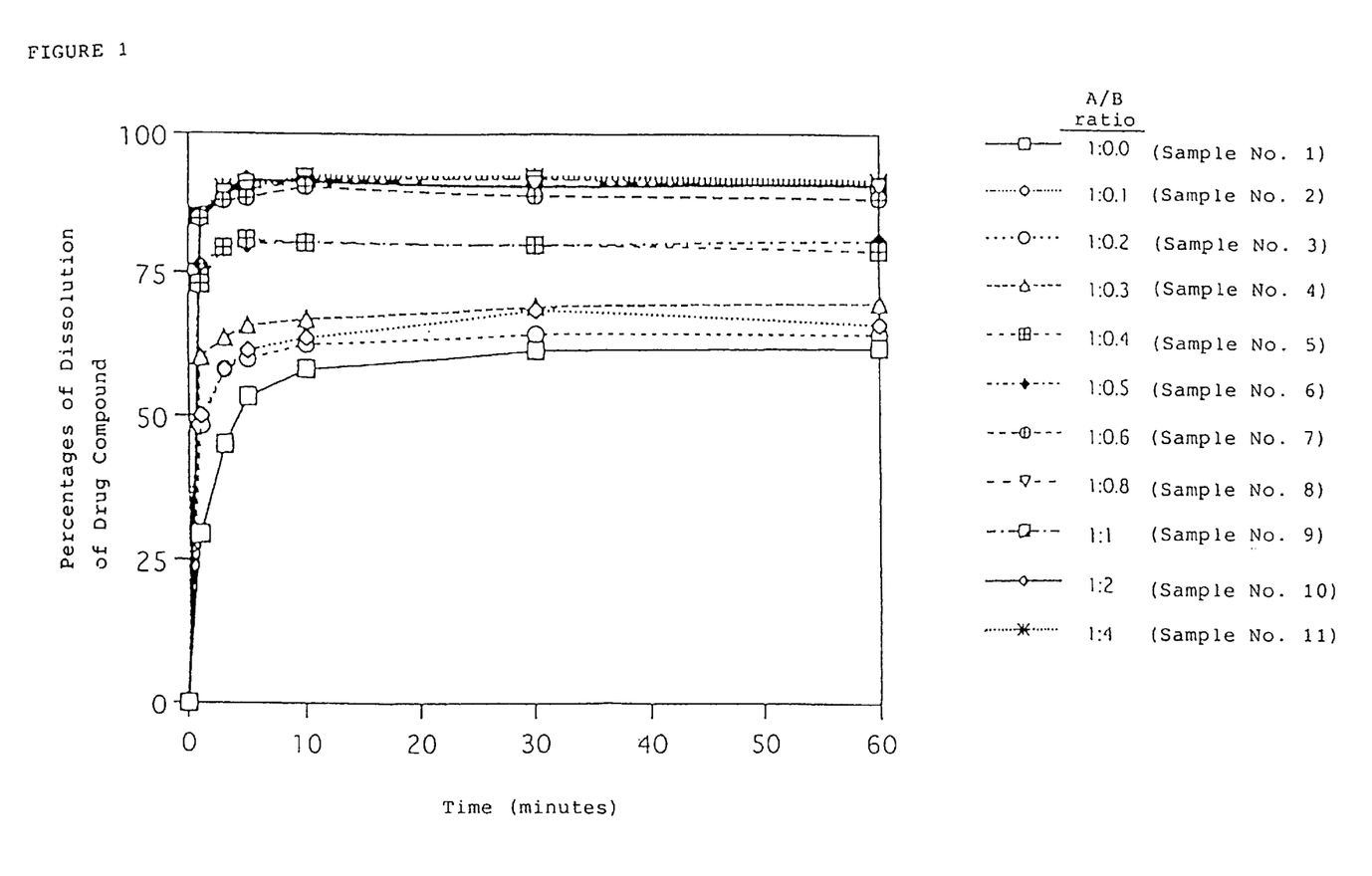
FIG. 1 shows a graph of representing that curves of changes in the percentages of dissolution of Cefditoren pivoxyl from the fine granules made of the composition as prepared in the following Example 1 of the first aspect invention, as well as from the similar but comparative fine granules containing no casein salt are plotted against the time (minutes) lapsed.

The above numerical figures of Table 2 are plotted in FIG. 1 of the accompanying drawings so as to depict a graph of representing the curves which show that the percentages of the dissolution of the drug compound, Cefditoren pivoxyl, in water were changing with the laps of time.

From the curves of FIG. 1, it will be seen that the concentration of Cefditoren pivoxyl dissolved in water, as well as the percentages of the dissolution of this drug compound were enhanced with the increasing proportions of sodium caseinate incorporated per 1 proportion of the drug compound, and that the percentages of the dissolution of the drug compound reached a substantially constant value when the ratio of Cefditoren pivoxyl to sodium caseinate (the A/B ratio) is at 1:0.5 or more.

In more details, from the numerical test results of Table 2 above, it can further be observed that, for instance, the sample No. 2 (the A/B ratio of 1:0.1) showed the values of 61.28% and 63.55% for the percentages of the dissolution of the drug compound, respectively, at the times of measurement of 5 minutes and 10 minutes as the lapse time, whilst the sample No. 1, (the comparative, the A/B ratio of 1:0.0) showed the values of 53.31% and 58.15%, respectively, for the percentages of the dissolution of the drug compound at the same measurment times. This reveals that the sample No. 2 according to the first aspect of this invention is able to obtain an increase by about 15% in the percentages of the dissolution of Cefditoren pivoxyl at the lapse time of 5 minutes over the comparative sample No. 1 containing no sodium caseinate [by calculating from an equation of (61.28−53.31)/53.31×100=14.9%] and is also able to obtain an increase of about 9.3% in the percentages of the dissolution of Cefditoren pivoxyl at the lapse time of 10 minutes over the comparative sample No. 1 [by calculating from an equation of (63.55−58.15)/58.15×100=ca.9.3%]. It can again be observed that, for instance, the sample No. 5 (the A/B ratio of 1:0.4) according to the first aspect of this invention showed the value of 81.02% for the percentages of the dissolution of Cefditoren pivoxyl as measured at the lapse time of 5 minutes, to reveal that the sample No. 5 is able to obtain an increase of about 52% in the percentages of the dissolution of Cefditoren pivoxyl over the comparative sample No. 1 at the lapse time of 5 minutes [by calculating from an equation of (81.02−53.31)/53.31×100= 51.96%].

TEST EXAMPLE 2

Each product of the tablets produced in Examples 2 to 8 as well as in Referential Example 2 above was subjected to the Dissolution Test presribed in the Japanese Pharmacopeia, the 13th-Edition, with using a purified water prepared by distillation, as the dissolution medium, and with using the apparatus formed from a cylinderical vessel having a hemispherical bottom and provided with a paddle-like stirrer.

The tablets under test were placed into the pool of the purified water in said vessel which was agitated by the aforesaid stirrer. Immediately after the addition of the tablets to the water pool, percentages of the dissolution of the drug compound (Cefditoren pivoxyl) from the tablets under test into water were measured with lapse of time from the addition of the tablets into the water medium to 60 minutes thereafter.

The test was made in 3 replications, and the results obtained were evaluated as an average.

Figure 2:
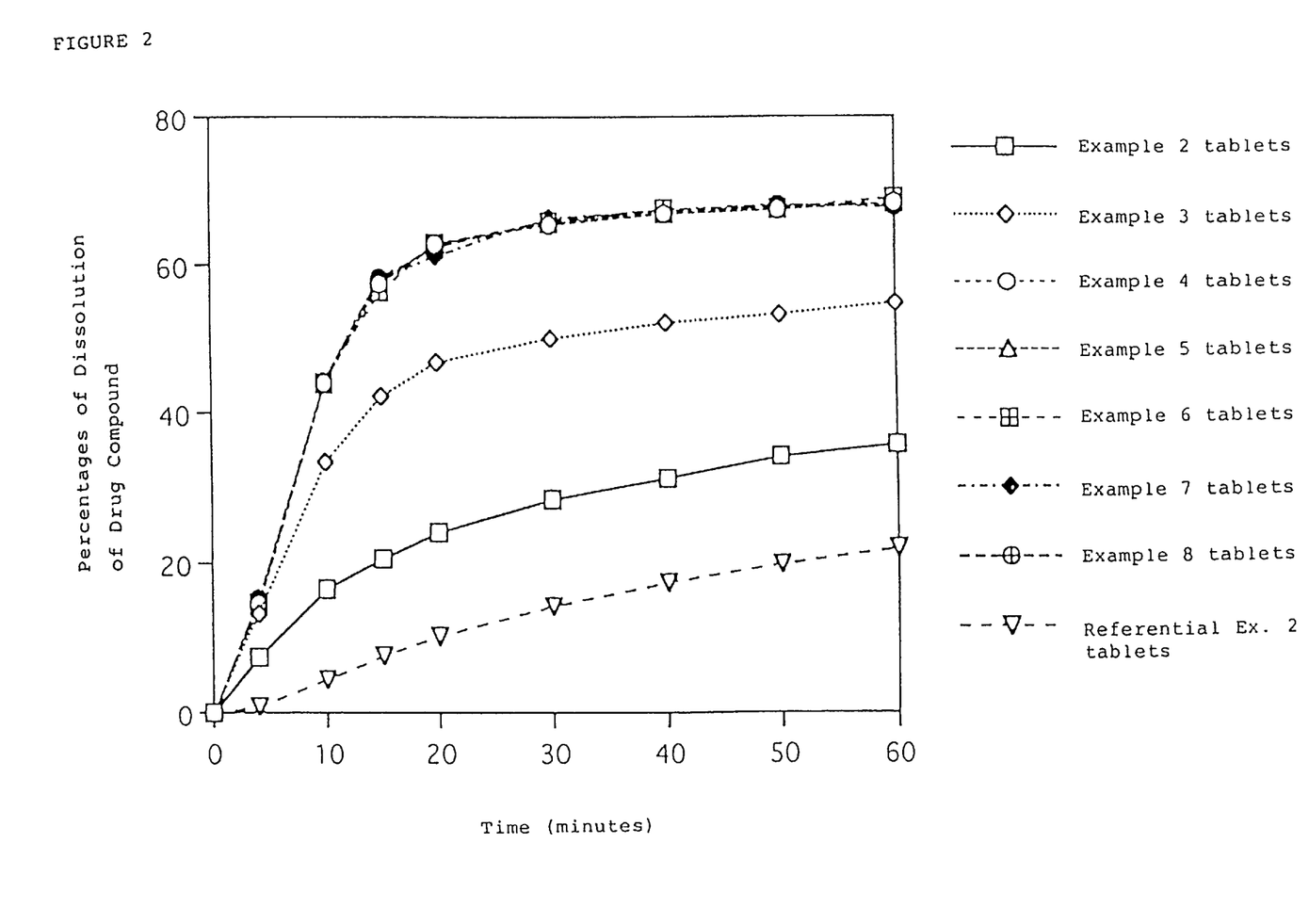
FIG. 2 shows a graph of representing that curves of changes in the percentages of dissolution of Cefditoren pivoxyl from the tablets made of the compositions prepared in the following Examples 2 to 8 of the first aspect invention, as well as from the similar but comparative tablets without casein salt as prepared in the following Referential Example 2 are plotted against the time (minutes) lapsed.

The test results (as the average) so obtained are plotted in FIG. 2 of the accompanying drawings so as to depict a graph of representing the curves which show that the percentages of the dissolution of Cefditoren pivoxyl were changing with the lapse time (in minutes).

Each product of the tablets produced in Examples 2 to 8 as well as the product of the comparative tablets produced in Referential Example 2 above showed such values of 35.55%, 54.52%, 68.23%, 68.11%, 68.84%, 67.98%, 67.56% and 21.82%, respectively, at the measurement time of the lapse time of 60 minutes.

As will be apparent from the curves of FIG. 2, it is found that the ratio of Cefditoren pivoxyl to sodium caseinate is at a value of 1:0.4 or more in the tablets under test, the properties of the dissolution of Cefditoren pivoxyl from the tablets can be improved remarkably over those of the comparative tablets containing no sodium caseinate, and that the effects of the improvement in the properties of the dissolution of Cefditoren pivoxyl are of the same extent as above when the ratio of Cefditoren pivoxyl to sodium caseinate is at a value of 1:2.

TEST EXAMPLE 3

This Example is to test and demonstrate evidently that the composition according to the first aspect of this invention is able to attain an excellent effect of improvement in the oral absorbability of Cefditoren drug. For this purpose, the absorbability of the Cefditoren component at the digestive tubes was estimated with using Beagle dogs as the test animal when the composition of this invention was orally given to the dogs. Test procedure: Each product of the tablets produced in Example 4 as well as in Referential Examples 1 and 2 above were employed for the tests. To the dogs weighing approximately 10 kg (female) which had been prohibited from drinking and eating for 16 hours, one tablet under test was orally administered to one dog together with 30 ml of water at such a dosage equivalent to 130 mg of Cefditoren pivoxyl per one dog. After the oral administration, plasma samples were taken and collected from the dog intermittently at the times of lapse of 0.25, 0.5, 1, 2, 4, 6 and 8 hours from the administration. The concentration ($\mu$g/ml) of the Cefditoren component present in the plasma samples so collected was determined according to a high performance liquid chromatographic method. The test was done in 5 replications, and the results obtained were evaluated as a mean value.

Figure 3:
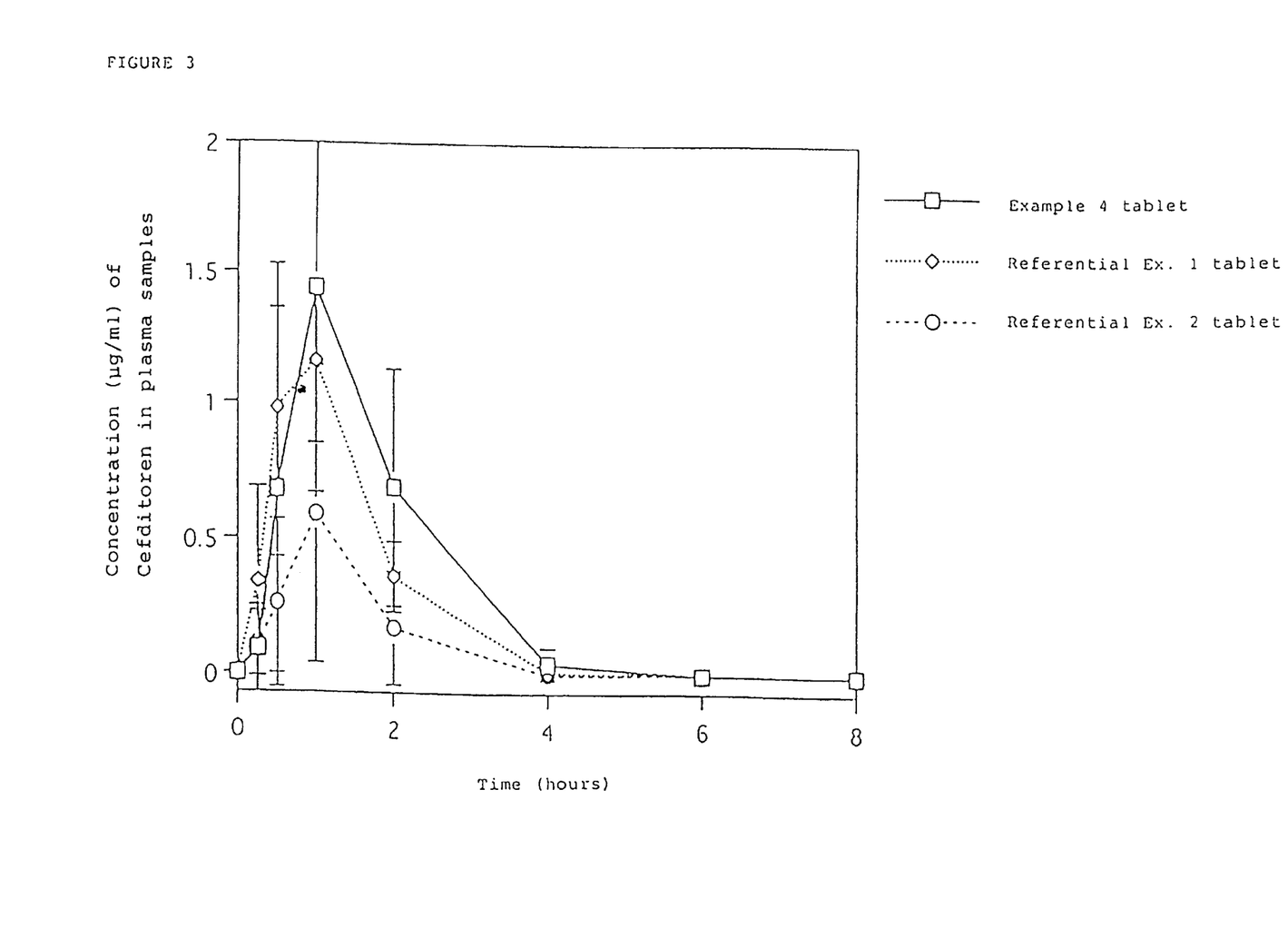
FIG. 3 shows a graph of representing that the curves of changes in the concentration ($\mu$g/ml) of Cefditoren in the plasma samples are plotted against the time (hours) lapsed, when the plasma samples have been taken from such Beagle dogs which received oral administration of the tablets as prepared in the following Example 4 of the first aspect invention or which received oral administration of similar but comparative tablets as prepared in the following Referential Examples 1 to 2 not according to this invention.

The test results (as the mean values) so obtained are plotted in FIG. 3 of the accompanying drawings so as to depict a graph of representing the curves which shows that the concentration ($\mu$g/ml) of Cefditoren present in the plasma samples was changing with the lapse of time (hours). The test results obtained showed that the tablets produced in Example 4 from the composition of this invention comprising the mixture of Cefditoren pivoxyl, sodium caseinate, D-mannitol and croscarnellose sodium and having the ratio of Cefditoren pivoxyl to sodium caseinate of 1:0.4 could give a mean value of approx. 1.4 $\mu$g/ml of Cefditoren in the plasma sample as collected at the time of 1 hour from the oral administration of the tablet, whilst the comparative tablets produced in Referential Examples 1 and 2 could give mean values of approx. 1.15 $\mu$g/ml and 0.6 $\mu$g/ml of Cefditoren, respectively, in the plasma samples as collected at the time of 1 hour from the oral administration of these comparative tablets.

It can be observed from FIG. 3 that the sodium caseinate-containing composition of Example 4 according to this invention is able to attain a significant enhancement in the absorbability of the Cefditoren component at the digestive tubes, in comparison with the comparative tablets of Referential Example 2 having a usual formulation.

Besides, the effect of the significant enhancement in the oral absorbability of Cefditoren which was attained with the tablets of Example 4 is shown to be higher than an effect such that the absorbability of Cefditoren can be enhanced with the comparative tablets of Referential Example 1 by admixing Cefditoren pivoxyl with $\beta$-cyclodextrin according to the known art of enhancing the oral absorbability of Cefditoren as described in the aforesaid Japanese patent appln. first publication "Kokai" No. Hei-1-268637 etc.

It can also be observed that the effect of enhancement in the oral absorbability of Cefditoren can be obtained by the addition of sodium caseinate to the same degree as or a degree higher than that obtained by the addition of the $\beta$-cyclodextrin, even when the amount of sodium caseinate added is decreased to a half or less than the half of the amount of the $\beta$-cyclodextrin added.

For these reasons, this invention can make it possible to produce a tablet preparation of Cefditoren pivoxyl which is of smaller sizes and much more easily administrable per os than the tablets of said Referential Example 1.

TEST EXAMPLE 4

This Example is to conduct the tests of functionality to examine the bitter taste which is exhibited by the fine granules of Example 9 and also by the fine granules of Referential Example 3 above.

Thus, a 1 g-portion of the respective granules under test was placed along with 5 ml of water into the mouth of each person of the testing panel (the panelists) and kept for 10 seconds within the mouth, and thereafter the whole of the granule and water were vomitted from the mouth. The degree of the bitter taste then felt was estimated and classified in three levels of "slightly bitter", "bitter" and "very much bitter", which were given, in order, with scores of 1, 2 and 3, respectively. In these tests, it is so arranged that the 10 panelists were divided equally into two groups, that the first group comprising the five panelists carried out the estimation of the bitter taste of the granules of Example 9, then rinsed their mouth well with a large amount of water, and 30 minutes later they tried the estimation of the bitter taste of the other granules of Referential Example 3, and also that the second group comprising the five panelists carried out the estimation of the bitter taste of the granules of Referential Example 3, then rinsed their mouth well with a large amount of water, and 30 minutes later they tried the estimation of the bitter taste of the other granules of Example 9.

The results so obtained of the functionality tests are shown in Table 3 below. It was made evident that the granules of the composition of this invention set forth in Example 9 had a reduced bitter taste, as compared with that of the granules of Referential Example 3.

TABLE 3

| Panelist No. | Scores of estimation of bitter taste | |
| --- | --- | --- |
| | Granules of Example 9 | Granules of Referential Ex. 3 |
| First group | | |
| No. 1 | 1 | 2 |
| No. 2 | 1 | 1 |
| No. 3 | 1 | 2 |
| No. 4 | 1 | 2 |
| No. 5 | 2 | 2 |
| Second group | | |
| No. 6 | 1 | 2 |
| No. 7 | 1 | 1 |
| No. 8 | 1 | 2 |
| No. 9 | 2 | 2 |
| No. 10 | 1 | 1 |
| Mean value ± S.D. | 1.2 ± 0.4* | 1.7 ± 0.5* |

Notes:
S.D. means the standard deviation.
The mark * denotes that the two mean values given were significant with a risk rate of 5%.

Further, this invention in the second aspect thereof is now illustrated with reference to the following Examples 10 to 12 and Test Examples 5 to 6, in order to demonstrate that the composition according to the second aspect of this invention is also capable of maintaining the high rate of the dissolution of Cefditoren pivoxyl from the composition after the storage at an elevated temperature.

EXAMPLES 10–12

A uniform powdery mixture comprising Cefditoren pivoxyl, sodium caseinate, D-mannitol and croscarmellose sodium in the same proportions of the constituents as set out in Example 4 above and having the ratio of Cefditoren pivoxyl to sodium caseinate of 1:0.4 was prepared. Said mixture was then added with an aqueous solution of 0.007% by weight of a commercially available sodium polyphosphate (containing sodium tri-polyphosphate as the main constituent) in such proportions of said aqueous solution that the 1 mg, 2 mg or 3 mg of said sodium polyphosphate would be present in each of the tablets which were produced finally.

The resulting admixtures so prepared by the addition of the aqueous sodium polyphosphate to said powdery mixture were then wet-granulated in the same manner as in Example 4. The granules so obtained were further added with magnesium stearate and shaped into tablets in the same manner as in Example 4. Thereby, there were produced according to the second aspect of this invention three sorts of the tablets having the weight ratios of sodium caseinate to sodium polyphosphate of 1:0.02, 1:0.04 and 1:0.06, respectively, at a scale of 1000 tablets.

REFERENTIAL EXAMPLES 4 and 5

A uniform powdery mixture comprising Cefditoren pivoxyl, sodium caseinate, D-mannitol and croscarmellose sodium in the same proportions of the formulation as set out in Example 4 and having the weight ratio of Cefditoren pivoxyl to sodium caseinate of 1:0.4 was prepared similarly to Examples 10–12.

The resulting powdery mixture was then added and mixed with an aqueous solution of 0.007% by weight of the sodium polyphosphate (comprising sodium tri-polyphosphate as the main constituent) in such proportions of said aqueous solution that 5 mg or 20 mg of the sodium polyphosphate would be present in each of the tablets which were produced finally.

The admixtures so obtained by the addition of the aqueous sodium polyphosphate to said powdery mixture were then wet-granulated in the same manner as in Example 4. The resulting granules were further admixed with magnesium stearate and then shaped into tablets in the same manner as in Example 4. Thereby, there were produced two sorts of the tablets having the weight ratios of sodium caseinate to sodium polyphosphate of 1:0.1 and 1:0.4, respectively, at a scale of 1000 tablets.

TEST EXAMPLE 5

Immediately after the production of the tablets of Example 4 according to the first aspect of this invention, as well as immediately after the production of the tablets of Examples 10 and 12 according to the second aspect of this invention, these tablets were tested by the test procedure of the Dissolution Test prescribed in the Japanese Pharmacopeis, the 13th-Edition, to measure their percentages of the dissolution of the drug component (Cefditoren pivoxyl) from the tablets into water. Also, after these tablets had been stored in sealed containers at 40° C. for 3 months, the so stored tablets were tested by the same test procedure of the Dissolution Test.

The procedure of this Dissolution Test comprised using an apparatus formed from a cylindrical vessel having a hemispherical bottom and provided with a paddle-type stirrer, placing the tablets under test into a pool of 900 ml of water in said vessel, then stirring the water pool at 37° C. by means of the stirrer at 50 rpm., and measuring the concentration of Cefditoren pivoxyl in the water with lapse of time (minutes) and evaluating the percentages of the dissolution of Cefditoren pivoxyl in water in a manner similarly to Test Example 1 given hereinbefore.

The test was done in 3 replications, and the test results obtained were evaluated as the mean values with standard deviations. The results obtained are tabulated in Table 4 below.

TABLE 4

| Test samples | Mean value of % of the dissolution of drug compound Lapse time (min) | | | |
| --- | --- | --- | --- | --- |
| | 10 | 15 | 20 | 40 |
| Tablets of Ex. 4 immediately after their production | 43.5 | 55.5 | 57.3 | 60.0 |
| Tablets of Ex. 4 after their storage | 28.8 | 36.0 | 38.1 | 41.8 |
| Tablets of Ex. 10 immediately after their production | 44.3 | 52.4 | 54.0 | 54.8 |
| Tablets of Ex. 10 after their storage | 43.0 | 49.5 | 51.2 | 52.2 |
| Tablets of Ex. 12 immediately after their production | 38.5 | 50.4 | 54.0 | 55.1 |
| Tablets of Ex. 12 after their storage | 41.3 | 51.5 | 53.5 | 53.8 |

Figure 4:
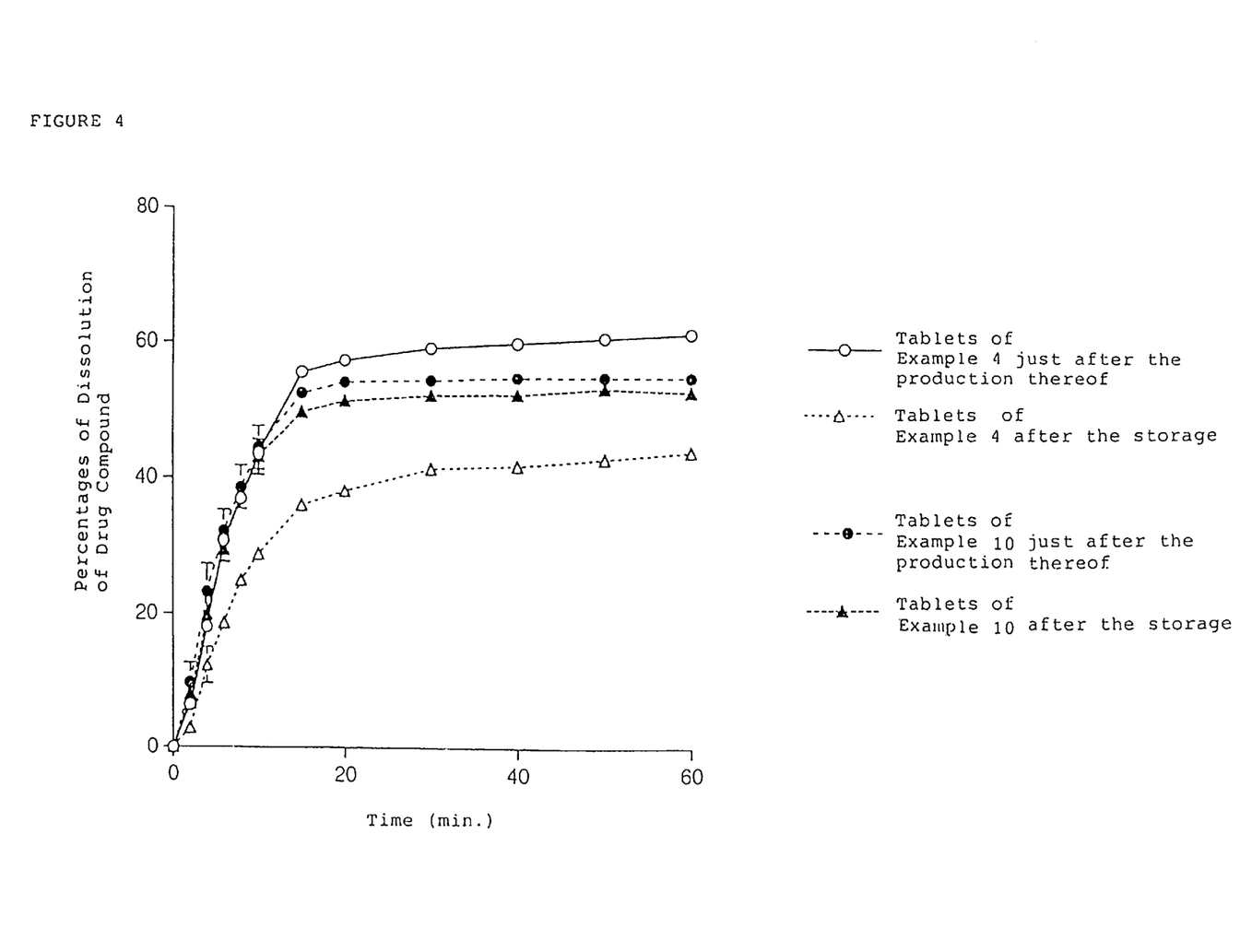
FIG. 4 shows a graph of representing that the curves of changes in the percentages of dissolution of Cefditoren pivoxyl from the tablets as produced in the Example 4 according to the first aspect of this invention, as well as from the tablets as produced in the following Example 10 according to the second aspect of this invention are plotted against the time (in minutes) lapsed, when the measurements of the changes in the percentages of dissolution of Cefditoren pivoxyl from the tablets are done immediately after the production of the tablets under test and also after the storage of the tablets under test at 40° C. for 3 months.
Figure 5:
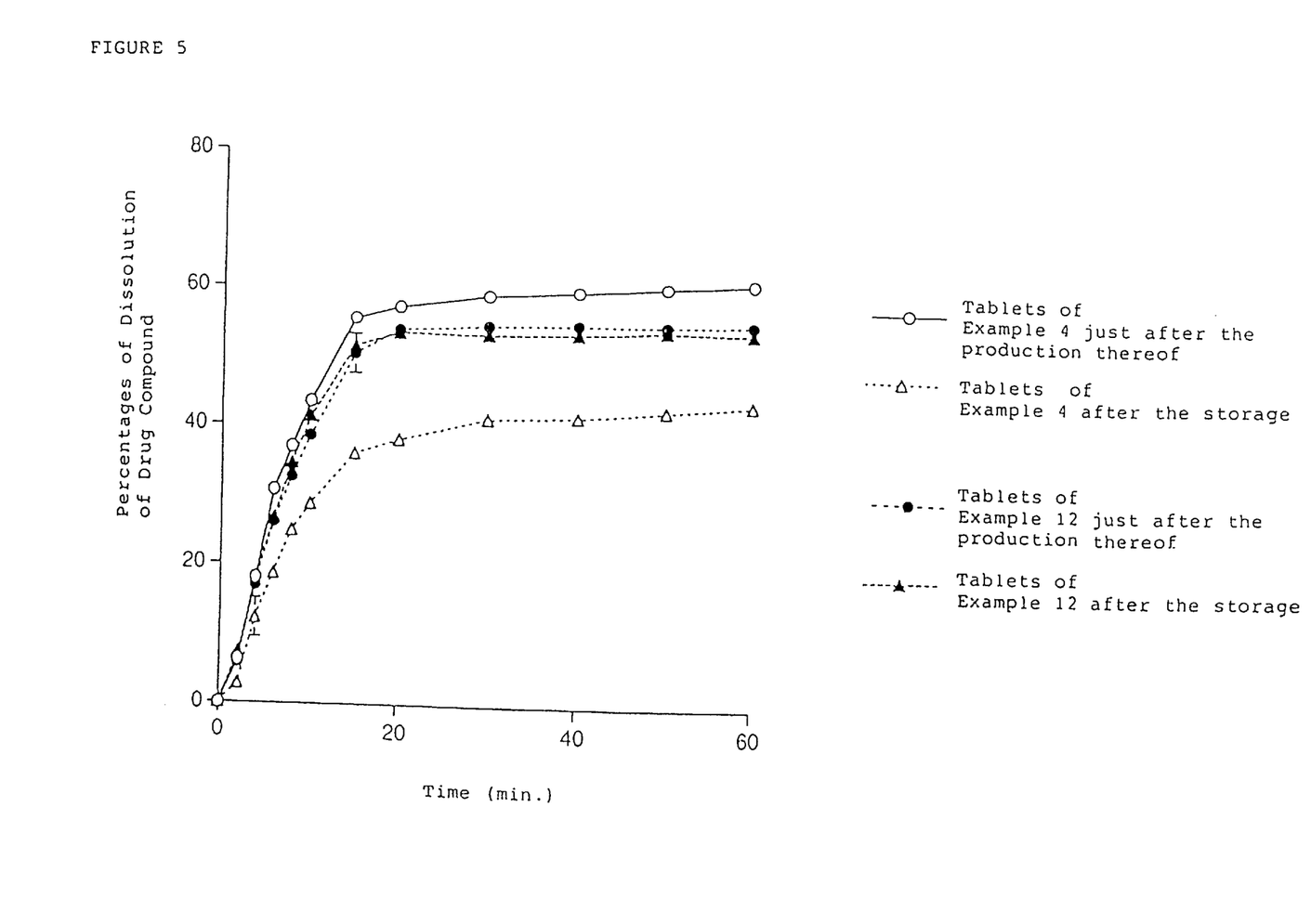
FIG. 5 shows a graph of representing that the curves of changes in the percentages of dissolution of Cefditoren pivoxyl from the tablets as produced in the Example 4 according to the first aspect of this invention, as well as from the tablets as produced in the following Example 12 according to the second aspect of this invention are plotted against the time (in minutes) lapsed, when the measurements of the percentages of dissolution of Cefditoren pivoxyl from the tablets under test are done immediately after the production of the tablets under test and also after the storage of the tablets under test at 40° C. for 3 months.

The test results of Table 4 above are plotted in FIG. 4 and FIG. 5 of the accompanying drawings so as to depict the curves which show that the percentages of the dissolution of Cefditoren pivoxyl in water from the tablets of the respective test samples were changing with lapse of time (minutes).

As will be apparent from the curves of FIG. 4 and FIG. 5, it is observed that the tablets of Example 4 containing no sodium polyphosphate had bring about a considerable reduction in their mean value of the percentages of the dissolution of Cefditoren pivoxyl therefrom after they had been stored under the severe conditions at 40° C. for 3 months. In contrast, it is observed that the tablets of Examples 10 and 12 which contained 1 mg and 3 mg of the sodium polyphosphate, respectively, per one tablet, are prevented from bringing about any substantial reduction in their percentages of the dissolution of Cefditoren pivoxyl therefrom even after they had been stored at 40° C. for three months.

TEST EXAMPLE 6

The tablets of Example 4 and Examples 10–12, as well as the tablets of Referential Examples 4–5 were tested by the test procedure of the Disintegration Test prescribed in the Japanese Pharmacopeia, the 13th-Edition, in respect of their disintegratability of the tablets which were placed in a volume of water at 37° C. and in a volume of the 1st fluid of the Disintegration Test prescribed in the Japanese Pharmacopeia, the 13th-Edition (namely, an artificial stomack juice, pH 1.2, set forth in said Japanese Pharmacopeia) at 37° C., respectively.

The disintegratability of the tablets are evaluated in term of the time (minutes) which was required for that the six tablets were placed in the pool of the water medium or the 1st fluid of the Disintegration Test, then agitated by upwards and downwards movements and consequently disintegrated and completely dispersed in the liquid medium so that any visual solid particles could not be observed in the liquid medium.

The test results obtained were evaluated as the mean values and tabulated, in Table 5 below.

TABLE 5

| Tablets tested of Examples | Amount (mg) of sodium polyphosphate per one tablet | Weight ratio of sodium caseinate to sodium polyphosphate | Disintegratability (in minutes) | |
|---|---|---|---|---|
| | | | In water | In the 1st fluid of the Disintegration Test |
| Example 4 | 0 | 1:0 | 11.8 | 9.7 |
| Example 10 | 1 | 1:0.02 | 11.4 | 9.0 |
| Example 11 | 2 | 1:0.04 | 10.9 | 9.4 |
| Example 12 | 3 | 1:0.06 | 14.2 | 10.0 |
| Referential Example 4 | 5 | 1:0.1 | 17.1 | 10.7 |
| Referential Example 5 | 20 | 1:0.4 | 20.5 | 28.4 |

From the test results of Table 5 above, it is observed that the tablets of Examples 10 and 11 had an improved disintegratability over that of the tablets of Example 4, while the tablets of Example 12 had a substantial reduction in their disintegratability, as compared to the tablets of Example 4. It can also be seen that the tablets of Referential Examples 4 and 5 containing sodium polyphosphate at a higher ratio of sodium caseinate to sodium polyhosphate of 1:0.1 or 1:0.4 showed a disintegratability remarkably reduced, in comparison with the tablets of Example 4.

INDUSTRIAL APPLICAPABILITY

As will be clear from the foregoing discriptions of the subjects of the first aspect of this invention as well as the second aspect of this invention, the compositions according to this invention have advantages that the bitter taste of Cefditoren pivoxyl is reduced, the solubilities of Cefditoren pivoxyl are enhanced and also the oral absorbability of Cefditoren pivoxyl is improved. Accordingly, the compositions of this invention are useful in that these compositions of this invention can provide orally administrable preparations of Cefditoren pivoxyl which can readily be given via the oral route.

We claim:

1. An antibacterial composition of Cefditoren pivoxyl for use in oral administration and having a reduced bitter taste and having an enhanced dispersibility of the composition in water and an enhanced rate of dissolution of Cefditoren pivoxyl component in water, characterised in that the composition comprises a mixture of Cefditoren pivoxyl with a proportion of a pharmaceutically acceptable and water-soluble casein salt.

2. The composition as claimed in claim 1, in which the casein salt is sodium caseinate or potassium caseinate.

3. The composition as claimed in claim 1, in which the ratio by weight of Cefditoren pivoxyl to the casein salt is in a range of 1:0.1 to 1:4.

4. The composition as claimed in claim 3, in which the ratio by weight of Cefditoren pivoxyl to the casein salt is in a range of 1:0.4 to 1:2.

5. The composition as claimed in claim 1, which further contains one or more additives chosen from pharmaceutically acceptable excipients and disintegrators.

6. The composition as claimed in claim 1, which is prepared in the form of granules, fine granules or tablets.

7. An antibacterial composition of Cefditoren pivoxyl for use in oral administration and having a reduced bitter taste and having an enhanced dispersibility of the composition and an enhanced rate of dissolution of the Cefditoren pivoxyl component in water and also capable of maintaining a high rate of disolution of the Cefditoren pivoxyl component into water after storage of the composition at an elevated temperature, characterized in that the composition comprises a mixture of Cefditoren pivoxyl with a proportion of a pharamceutically acceptable and water-soluble casein salt and a proportion of a pharmaceutically acceptable and water-soluble polyphosphoric acid salt.

8. The composition as claimed in claim 7, in which the casein salt is sodium caseinate or potassium caseinate and the polyphosphoric acid salt is sodium or potassium polyphosphate.

9. The composition as claimed in claim 8, in which the sodium or potassium polyphosphate is a pure sodium or potassium tri-polyphosphate, or a commercially available sodium or potassium polyphosphate.

10. The composition as claimed in claim 7, in which the ratio by weight of the casein salt to polyphosphoric acid salt is in a range of 1:0.02 to 1:0.06.

11. The composition as claimed in claim 7, in which the ratio by weight of Cefditoren pivoxyl to the casein salt is in a range of 1:0.1 to 1:4.

12. The composition as claimed in claim 7, which further contains one or more additives chosen from pharmaceutically acceptable excipients and disintegrators and is prepared in the form of granules, fine granuels or tablets.

13. The composition as claimed in claim 7, in which the ratio by weight of the casein salt to polyphosphoric acid salt is in a range of 1:0.02 to 1:0.05.

14. A method for reducing the bitter taste of Cefditoren pivoxyl and enhancing the rate of dissolution of Cefditoren pivoxyl into water, as well as the concentration of Cefditoren pivoxyl attainable by its dissolution into water for a predetermined period of time, which method comprises mixing Cefditoren pivoxyl with a proportion of a pharmaceutically acceptable and water-soluble casein salt at a ratio by weight of Cefditoren pivoxyl to the casein salt in a range of 1:0.1 to 1:4 and thereby forming a uniform mixture of Cefditoren pivoxyl with the casein salt.

15. The method as claimed in claim 14, in which the casein salt is sodium caseinate or potassium caseinate.

16. The method as claimed in claim 14, in which Cefditoren pivoxyl is mixed with the casein salt in a range of 1:0.4 to 1:2.

* * * * *